US011672841B2

(12) United States Patent
Wilson

(10) Patent No.: US 11,672,841 B2
(45) **Date of Patent: *Jun. 13, 2023**

(54) METHODS FOR TREATING HEART DISEASE IN A SUBJECT WITH FRIEDREICH'S ATAXIA BY AN AROMATIC-CATIONIC PEPTIDE

(71) Applicant: Stealth BioTherapeutics Inc., Needham, MA (US)

(72) Inventor: D. Travis Wilson, Newton, MA (US)

(73) Assignee: STEALTH BIOTHERAPEUTICS INC., Needham, MA (US)

(*) Notice: Subject to any disclaimer, the term of this patent is extended or adjusted under 35 U.S.C. 154(b) by 188 days.

This patent is subject to a terminal disclaimer.

(21) Appl. No.: 17/084,893

(22) Filed: Oct. 30, 2020

(65) Prior Publication Data

US 2021/0220431 A1 Jul. 22, 2021

Related U.S. Application Data

(63) Continuation of application No. 16/425,892, filed on May 29, 2019, now Pat. No. 10,835,573, which is a continuation of application No. 15/697,648, filed on Sep. 7, 2017, now abandoned, which is a continuation of application No. 14/908,053, filed as application No. PCT/US2014/049633 on Aug. 4, 2014, now abandoned.

(60) Provisional application No. 61/861,806, filed on Aug. 2, 2013.

(51) Int. Cl.

| | |
|---|---|
| ***A61K 38/00*** | (2006.01) |
| ***A61K 38/18*** | (2006.01) |
| ***A61K 38/19*** | (2006.01) |
| ***A61K 38/17*** | (2006.01) |
| ***C07K 14/475*** | (2006.01) |
| ***C07K 14/48*** | (2006.01) |
| ***C07K 5/00*** | (2006.01) |
| ***C07K 7/00*** | (2006.01) |
| ***A61K 38/07*** | (2006.01) |
| ***A61K 45/06*** | (2006.01) |
| ***A61K 38/28*** | (2006.01) |
| ***A61K 31/122*** | (2006.01) |
| ***A61K 31/401*** | (2006.01) |
| ***A61K 31/4412*** | (2006.01) |
| ***A61K 31/7048*** | (2006.01) |
| ***C07K 5/11*** | (2006.01) |
| *A61P 43/00* | (2006.01) |
| *A61P 21/00* | (2006.01) |
| *A61Q 19/08* | (2006.01) |
| *G01N 33/68* | (2006.01) |
| *C07K 5/10* | (2006.01) |
| *A61K 9/50* | (2006.01) |
| *A61P 25/28* | (2006.01) |

(52) U.S. Cl.

CPC ............ *A61K 38/07* (2013.01); *A61K 31/122* (2013.01); *A61K 31/401* (2013.01); *A61K 31/4412* (2013.01); *A61K 31/7048* (2013.01); *A61K 38/28* (2013.01); *A61K 45/06* (2013.01); *C07K 5/1019* (2013.01); *A61K 9/5052* (2013.01); *A61K 2300/00* (2013.01); *A61P 21/00* (2018.01); *A61P 25/28* (2018.01); *A61P 43/00* (2018.01); *A61Q 19/08* (2013.01); *C07K 5/10* (2013.01); *G01N 33/68* (2013.01); *G01N 2800/2835* (2013.01)

(58) Field of Classification Search

CPC .... A61K 2300/00; A61K 38/00; A61K 38/04; A61K 38/07; A61K 31/00; A61K 38/03; A61K 38/06; A61K 8/64

See application file for complete search history.

(56) References Cited

U.S. PATENT DOCUMENTS

| | | | | |
|---|---|---|---|---|
| 4,522,811 | A | 6/1985 | Eppstein et al. | |
| 5,674,534 | A | 10/1997 | Zale et al. | |
| 5,716,644 | A | 2/1998 | Zale et al. | |
| 6,468,798 | B1 | 10/2002 | Debs et al. | |
| 7,550,439 | B2 | 6/2009 | Szeto | |
| 7,576,061 | B2 | 8/2009 | Szeto et al. | |
| 10,835,573 | B2 * | 11/2020 | Wilson | A61K 31/7048 |
| 2011/0021562 | A1 | 1/2011 | Jenssen et al. | |
| 2011/0082084 | A1 * | 4/2011 | Szeto | C07K 5/1016 514/15.7 |

(Continued)

FOREIGN PATENT DOCUMENTS

| | | |
|---|---|---|
| CA | 2850520 | 4/2013 |
| CN | 107320711 | 11/2017 |

(Continued)

OTHER PUBLICATIONS

The factsheet of Friedreich Ataxoa from NINDS website:www.ninds.nih.gov/friedreich-ataxia-fact-sheet#3070_1 retrieved on Aug. 18, 2022.*

(Continued)

*Primary Examiner* — Chang-Yu Wang

(74) *Attorney, Agent, or Firm* — Foley & Lardner LLP

(57) ABSTRACT

The disclosure provides methods of preventing or treating Friedreich's ataxia in a mammalian subject, reducing risk factors, signs and/or symptoms associated with Friedreich's ataxia, and/or reducing the likelihood or severity of Friedreich's ataxia. The methods comprise administering to the subject an effective amount of an aromatic-cationic peptide to e.g., reduce oxidative stress, increase mitochondrial metabolism, or a combination thereof.

14 Claims, No Drawings

(56) References Cited

U.S. PATENT DOCUMENTS

2013/0109658 A1 5/2013 Testi et al.

FOREIGN PATENT DOCUMENTS

WO WO-96/40073 A2 12/1996
WO WO-99/15154 A1 4/1999
WO WO-00/38651 A1 7/2000
WO WO2018171278 * 9/2018

OTHER PUBLICATIONS

Widemann et al. (J. Neurochem. 2013; 126 (Suppl. 1): 88-93.*
Amselem, et al., "A Large-Scale Method for the Preparation of Sterile and Nonpyrogenic Liposomal Formulations of Defined Size Distributions for Clinical Use." Liposome Technology, 1993, vol. I, 2nd ed., CRC Press, pp. 502-525.
Andrew R. Blight, "Miracles and molecules—progress in spinal cord repair," Nat. Neurosci, 2002, pp. 1051-1054.
Calabrese, Vittorio et al., "Oxidative stress, mitochondrial dysfunction and cellular stress response in Friedreich's ataxia," J Neuro Sciences, (2005), vol. 233, Issues 1-2, pp. 145-162.
Chonn et al., "Recent Advances in Liposomal Drug-Delivery Systems," Curr. Opin. Biotechnol., Dec. 1995, vol. 6, Issue 6, pp. 698-708.
Final Office Action in U.S. Appl. No. 14/908,053 dated Mar. 9, 2017.
Gregoriadis, "Engineering Liposomes for Drug Delivery: progress and Problems," Trends in Biotechnology, Dec. 1995, vol. 13, No. 12, pp. 527-537.
Hart et al., "The use of animal models to investigate the pathogenesis of neuroinflammatory disorders of the central nervous system," Curr. Opin. Neurol. 2003, pp. 375-383.
Hoke, Ahmet, Mechanisms of Disease: what factors limit the success of peripheral nerve regeneration in humans? Nat. Clin. Pract. Neurol, 2006, pp. 448-454.
International Search Report and Written Opinion in International Patent Application No. PCT/US2014/049633 dated Dec. 11, 2014 (9 pages).
Kozarich, et al., "Next generation therapeutics: Looking to the horizon: Editorial overview," Curr. Opin. Chem. Biol., 1998, vol. 2, Issue 4, pp. 439-440.
Lichtenberg, et al., "Liposomes: Preparation, Characterization, and Preservation," Methods Biochem. Anal., 1998, vol. 33, pp. 337-462.
Mizuguchi, et al., "Intratumor administration of fusogenic liposomes containing fragment A of diphtheria toxin suppresses tumor growth." Cancer Lett., Feb. 26, 1996, vol. 100, Issue 1, pp. 63-69.
Non-Final Office Action in U.S. Appl. No. 14/908,053 dated Jun. 2, 2016.
Non-Final Office Action in U.S. Appl. No. 15/697,648 dated Nov. 30, 2018.
Non-Final Office Action in U.S. Appl. No. 16/425,892 dated Sep. 27, 2019.
Notice of Allowance in U.S. Appl. No. 16/425,892 dated Jul. 16, 2020.
Office Action in CA Patent Application No. 2920020 dated Apr. 30, 2020 (4 pages).
Puccio, Hélène et al., "Mouse models for Friedreich ataxia exhibit cardiomyopathy, sensory nerve defect and Fe—S enzyme deficiency followed by intramitochondrial iron deposits," Nature Genetics, (Feb. 2001), vol. 27, No. 2, pp. 181-186.
Reddy, "Controlled-Release, Pegylation, Liposomal Formulations: New Mechanisms in the Delivery of Injectable Drugs," Ann Pharmacother., Jul./Aug. 2000, vol. 34, pp. 915-923.
Schmidt et al., "Neural Tissue Engineering: Strategies for Repair and Regeneration," Annu. Rev. Biomed. Eng. 2003; pp. 293-347.
U.S. Office Action in U.S. Appl. No. 15/697,648 dated May 17, 2018.
Weiner, Alan L., "Liposomes for Protein Delivery: Selecting Manufacture and Development Processes," Immunomethods, Jun. 1994, vol. 4, No. 3, pp. 201-209.
Zhao, et al., "Transcellular Transport or a Highly Polar 3+ Net Charge Opioid Tetrapeptide," Journal of Pharmacology and Experimental Therapeutics, 2003, vol. 304, No. 1, pp. 425-432.
Office Action on CA Patent Application No. 2920020 dated Jun. 22, 2021 (6 pages).
Purroy et al., "Mitochondrial pore opening and loss of Ca2 exchanger NCLX levels occur after frataxin depletion", BBA—Molecular Basis of Disease, 2018, vol. 1864, pp. 618-631.
Sturm et al., "Friedreich's Ataxia, No Changes in Mitochondrial Labile Iron in Human Lymphoblasts and Fibroblasts", The Journal of Biological Chemistry, 2005, vol. 280(8), pp. 6701-6708.
Zhao et al., "Peptide SS-31 upregulates frataxin expression and improves the quality of mitochondria: implications in the treatment of Friedrich ataxia", Scientific Reports, 2017, vol. 7(9840), pp. 1-11.

* cited by examiner

METHODS FOR TREATING HEART DISEASE IN A SUBJECT WITH FRIEDREICH'S ATAXIA BY AN AROMATIC-CATIONIC PEPTIDE

CROSS-REFERENCE TO RELATED APPLICATIONS

This Application is a continuation of U.S. patent application Ser. No. 16/425,892, filed May 29, 2019, which is a continuation of U.S. patent application Ser. No. 15/697,648, filed Sep. 7, 2017, which is a continuation of U.S. patent application Ser. No. 14/908,053, filed Jan. 27, 2016, which is the U.S. 371 National Stage Application of PCT/2014/049633, filed Aug. 4, 2014, which claims the benefit of and priority to U.S. Application No. 61/861,806, filed Aug. 2, 2013, the entire contents of which are incorporated herein by reference in their entireties.

TECHNICAL FIELD

The present technology relates generally to compositions and methods for ameliorating or treating Friedreich's ataxia and/or reducing the severity of Friedreich's ataxia. In particular, the present technology relates to administering an effective amount of an aromatic-cationic peptide to a subject suffering from Friedreich's ataxia.

BACKGROUND

The following description is provided to assist the understanding of the reader. None of the information provided or references cited is admitted to be prior art to the compositions and methods disclosed herein.

Friedreich's ataxia is an inherited autosomal recessive disease that causes progressive damage to the nervous system. The ataxia results from the degeneration of nerve tissue in the spinal cord, in particular, sensory neurons essential for directing muscle movement of the arms and legs. The spinal cord becomes thinner and nerve cells lose some of their myelin sheath.

Friedreich's ataxia occurs when the FXN gene contains amplified intronic GAA repeats. The mutant FXN gene contains expanded GAA triplet repeats in the first intron; in a few pedigrees, point mutations have also been detected. Since the defect is located in an intron, which is removed from the mRNA transcript between transcription and translation, the mutated FXN gene does not result in the production of abnormal proteins. Instead, the mutation causes gene silencing, i.e., the mutation decreases the transcription of the gene, through induction of a heterochromatin structure in a manner similar to position-effect variegation.

The FXN gene encodes the protein frataxin. GAA repeat expansion causes frataxin levels to be reduced. Frataxin is an iron binding protein responsible for forming iron-sulphur clusters. One result of frataxin deficiency is mitochondrial iron overload.

SUMMARY

In one aspect, the present disclosure provides methods for treating or preventing Friedreich's ataxia, and/or treating or preventing the signs or symptoms of reduced levels of frataxin or frataxin activity in a subject in need thereof by administering to the subject a therapeutically effective amount of an aromatic-cationic peptide such as D-Arg-2',6'-Dmt-Lys-Phe-$NH_2$ or a pharmaceutically acceptable salt thereof.

In some embodiments, the subject displays reduced levels of frataxin compared to a normal control subject.

In some embodiments, the peptide is administered daily for 6 weeks or more. In some embodiments, the peptide is administered daily for 12 weeks or more.

In some embodiments, the subject has been diagnosed as having Friedreich's ataxia.

In some embodiments, the Friedreich's ataxia includes one or more of muscle weakness, loss of coordination, vision impairment, hearing impairment, slurred speech, curvature of the spine, diabetes, and heart disorders.

In some embodiments, the subject is human.

In some embodiments, the peptide is administered orally, topically, systemically, intravenously, subcutaneously, intraperitoneally, or intramuscularly In some embodiments, the method also includes separately, sequentially or simultaneously administering to the subject one or more agents selected from the group consisting of ACE inhibitors, digoxin, enalapril, or lisinopril, diuretics, beta blockers, idebenone, deferiprone, and insulin. In some embodiments, there is a synergistic effect between the peptide and the additional agent in this regard.

In some embodiments, the pharmaceutically acceptable salt comprises acetate or trifluoroacetate salt.

In one aspect, the present technology provides a method for reducing mitochondrial iron in a mammalian subject having or suspected of having Friedreich's ataxia, the method comprising: administering to the subject a therapeutically effective amount of the peptide D-Arg-2',6'-Dmt-Lys-Phe-$NH_2$ or a pharmaceutically acceptable salt thereof. In some embodiments, the mammalian subject has decreased expression of frataxin compared to a normal control subject. In some embodiments, the subject is human.

In some embodiments, the peptide is administered daily for 6 weeks or more. In some embodiments, the peptide is administered daily for 12 weeks or more.

In some embodiments, the Friedreich's ataxia comprises one or more of muscle weakness, loss of coordination, vision impairment, hearing impairment, slurred speech, curvature of the spine, diabetes, and heart disorders.

In some embodiments, the peptide is administered orally, topically, systemically, intravenously, subcutaneously, intraperitoneally, or intramuscularly In some embodiments, the method includes administering separately, sequentially or simultaneously to the subject one or more therapeutic agents selected from the group consisting of ACE inhibitors, digoxin, enalapril, or lisinopril, diuretics, beta blockers, idebenone, deferiprone, and insulin.

In some embodiments, the pharmaceutically acceptable salt comprises acetate or trifluoroacetate salt.

In some embodiments, the combination of peptide and an additional therapeutic agent has a synergistic effect in the reduction of mitochondrial iron and/or prevention or treatment of Friedreich's ataxia.

In one aspect, the present technology provides for methods for reducing the risk, signs or symptoms of Friedreich's ataxia in a mammalian subject having decreased expression of frataxin compared to a normal control subject. In some embodiments, the method includes administering to the subject a therapeutically effective amount of the peptide D-Arg-2',6'-Dmt-Lys-Phe-$NH_2$ or a pharmaceutically acceptable salt thereof.

In one aspect, the present technology provides for methods of stabilizing mitochondrial metabolism in a mammalian subject having or suspected of having Friedreich's ataxia and/or having lower than control or normal levels of frataxin. In some embodiments, the method includes administering to the subject a therapeutically effective amount of the peptide D-Arg-2',6'-Dmt-Lys-Phe-$NH_2$ or a pharmaceutically acceptable salt thereof.

In one aspect, the disclosure provides a method of treating or preventing Friedreich's ataxia in a mammalian subject, comprising administering to said mammalian subject a therapeutically effective amount of an aromatic-cationic peptide. In some embodiments, the aromatic-cationic peptide is a peptide having:

at least one net positive charge;

a minimum of four amino acids;

a maximum of about twenty amino acids;

a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1. In particular embodiments, the mammalian subject is a human.

In one embodiment, $2p_m$ is the largest number that is less than or equal to r+1, and may be equal to $p_t$. The aromatic-cationic peptide may be a water-soluble peptide having a minimum of two or a minimum of three positive charges.

In one embodiment, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In one embodiment, the peptide may have the formula Phe-D-Arg-Phe-Lys-$NH_2$ or 2',6'-Dmp-D-Arg-Phe-Lys-$NH_2$. In a particular embodiment, the aromatic-cationic peptide has the formula D-Arg-2',6'-Dmt-Lys-Phe-$NH_2$.

In one embodiment, the peptide is defined by formula I:

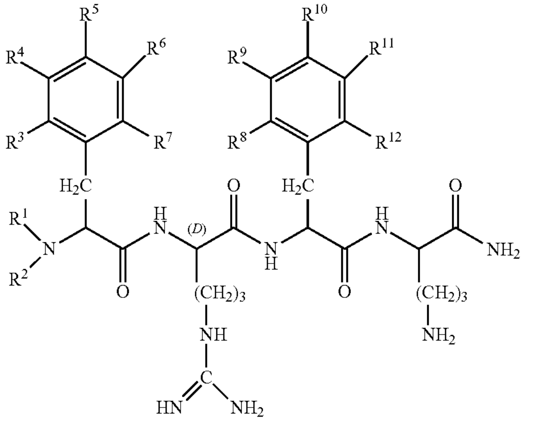

wherein $R^1$ and $R^2$ are each independently selected from (i) hydrogen;

(ii) linear or branched $C_1$-$C_6$ alkyl;

(iii)

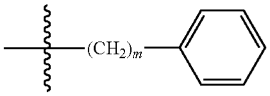

where m=1-3;

(iv)

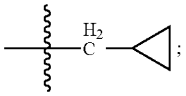

(v)

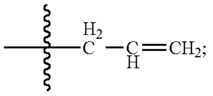

$R^3$, $R^4$, $R^5$, $R^6$, $R^7$, $R^8$, $R^9$, $R^{10}$, $R^{11}$ and $R^{12}$ are each independently selected from (i) hydrogen;

(ii) linear or branched $C_1$-$C_6$ alkyl;

(iii) $C_1$-$C_6$ alkoxy;

(iv) amino;

(v) $C_1$-$C_4$ alkylamino;

(vi) $C_1$-$C_4$ dialkylamino;

(vii) nitro;

(viii) hydroxyl;

(ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In one embodiment, the peptide is defined by formula II:

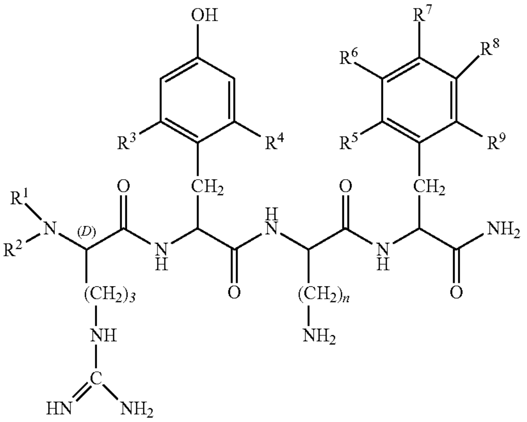

wherein $R^1$ and $R^2$ are each independently selected from (i) hydrogen;

(ii) linear or branched $C_1$-$C_6$ alkyl;

(iii)

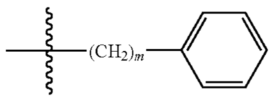

where m=1-3;

(iv)

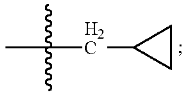 [SMILES: *CC1CC1]

(v)

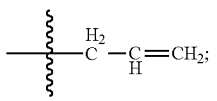

$R^3$ and $R^4$ are each independently selected from (i) hydrogen;

(ii) linear or branched $C_1$-$C_6$ alkyl;

(iii) $C_1$-$C_6$ alkoxy;

(iv) amino;

(v) $C_1$-$C_4$ alkylamino;

(vi) $C_1$-$C_4$ dialkylamino;

(vii) nitro;

(viii) hydroxyl;

(ix) halogen, where "halogen" encompasses chloro, fluoro, bromo, and iodo;

$R^5$, $R^6$, $R^7$, $R^8$, and $R^9$ are each independently selected from (i) hydrogen;

(ii) linear or branched $C_1$-$C_6$ alkyl;

(iii) $C_1$-$C_6$ alkoxy;

(iv) amino;

(v) $C_1$-$C_4$ alkylamino;

(vi) $C_1$-$C_4$ dialkylamino;

(vii) nitro;

(viii) hydroxyl;

(ix) halogen, where "halogen" encompasses chloro, fluoro, bromo, and iodo; and n is an integer from 1 to 5.

The aromatic-cationic peptides may be administered in a variety of ways. In some embodiments, the peptides may be administered orally, topically, intranasally, intravenously, subcutaneously, or transdermally (e.g., by iontophoresis).

DETAILED DESCRIPTION

It is to be appreciated that certain aspects, modes, embodiments, variations and features of the invention are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this technology belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "amino acid" includes naturally occurring amino acids and synthetic amino acids, as well as amino acid analogs and amino acid mimetics that function in a manner similar to the naturally-occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but those functions in a manner similar to a naturally occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g. an amount that reduces, ameliorates or delays the onset of the physiological symptoms of Friedreich's ataxia. In the context of therapeutic or prophylactic applications, in some embodiments, the amount of a composition administered to the subject will depend on the type and severity of the disease and on the characteristics of the individual, such as general health, age, sex, body weight and tolerance to drugs. In some embodiments, it will also depend on the degree, severity and type of disease. The skilled artisan will be able to determine appropriate dosages depending on these and other factors. The compositions can also be administered in combination with one or more additional therapeutic compounds. In the methods described herein, aromatic-cationic peptides, such as D-Arg-2'6'-Dmt-Lys-Phe-$NH_2$, or a pharmaceutically acceptable salt thereof, such as acetate or trifluoroacetate salt, may be administered to a subject having one or more signs, symptoms, or risk factors of Friedreich's ataxia, such as, e.g., muscle weakness, especially in the arms and legs, loss of coordination, motor control impairment, vision impairment, hearing impairment, slurred speech, curvature of the spine, diabetes, and heart disorders. For example, a "therapeutically effective amount" of the aromatic-cationic peptides includes levels at which the presence, frequency, or severity of one or more signs, symptoms, or risk factors of Friedreich's ataxia are reduced or eliminated. In some embodiments, a therapeutically effective amount reduces or ameliorates the physiological effects of Friedreich's ataxia, and/or the risk factors of Friedreich's ataxia, and/or delays the progression or onset of Friedreich's ataxia.

As used herein, "isolated" or "purified" polypeptide or peptide refers to a polypeptide or peptide that is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this definition.

As used herein, the terms "treating" or "treatment" or "alleviation" refers to therapeutic treatment, wherein the object is to reduce, alleviate or slow down (lessen) the targeted pathologic condition or disorder. By way of example, but not by way of limitation, a subject is successfully "treated" for Friedreich's ataxia if, after receiving a therapeutic amount of the aromatic-cationic peptides, such as D-Arg-2'6'-Dmt-Lys-Phe-$NH_2$, or a pharmaceutically acceptable salt thereof, such as acetate or trifluoroacetate salt, according to the methods described herein, the subject shows observable and/or measurable reduction in or absence of one or more signs and symptoms of Friedreich's ataxia, such as but not limited to, e.g., muscle weakness, especially in the arms and legs, loss of coordination, motor control impairment, vision impairment, hearing impairment, slurred speech, curvature of the spine, diabetes, and heart disorders. It is also to be appreciated that the various modes of treatment of medical conditions as described are intended to mean "substantial," which includes total but also less than total treatment, and wherein some biologically or medically relevant result is achieved. Treating Friedreich's ataxia, as used herein, also refers to treating the signs and symptoms related to reduced frataxin activity or frataxin expression levels characteristic of Friedreich's ataxia.

As used herein, "prevention" or "preventing" of a disease or condition, e.g., Friedreich's ataxia refers to results that, in a statistical sample, exhibit a reduction in the occurrence of the disorder or condition in the treated sample relative to an untreated control sample, or exhibit a delay in the onset of one or more symptoms of the disorder or condition relative to the untreated control sample. As used herein, preventing Friedreich's ataxia includes preventing or delaying the initiation of, preventing, delaying, or slowing the progression or advancement of Friedreich's ataxia. As used herein, prevention of Friedreich's ataxia also includes preventing a recurrence of one or more signs or symptoms of Friedreich's ataxia.

Aromatic-Cationic Peptides

The present technology relates to methods and compositions for preventing or treating Friedreich's ataxia in a subject in need thereof. In some embodiments, the methods and compositions prevent one or more signs or symptoms of Friedreich's ataxia in a subject. In some embodiments, the methods and compositions increase the level of frataxin expression in a subject. In some embodiments, the methods and compositions reduce the likelihood that a subject with risk factors for Friedreich's ataxia will develop one or more signs or symptoms of Friedreich's ataxia, or will delay the onset of Friedreich's ataxia. In some embodiments, the methods and compositions include an aromatic-cationic peptide such as D-Arg-2',6'-Dmt-Lys-Phe-$NH_2$, or a pharmaceutically acceptable salt thereof, such as acetate or trifluoroacetate salt.

It is known in the art that aromatic-cationic peptides of the present technology, such as D-Arg-2',6'-Dmt-Lys-Phe-$NH_2$, possess anti-oxidant properties, including the capacity to reduce the rate of lipid oxidation, peroxidation, mitochondrial $H_2O_2$ production, and intracellular reactive oxygen species (ROS) production. It is further known in the art that aromatic-cationic peptides of the present technology, such as D-Arg-2',6'-Dmt-Lys-Phe-$NH_2$, localize to the mitochondria, and have the capacity to inhibit caspase activation and apoptosis. It has also been shown that aromatic-cationic peptides, such as D-Arg-2',6'-Dmt-Lys-Phe-$NH_2$, restore mitochondria membrane potential. These and other properties of aromatic-cationic peptides of the present technology, such as D-Arg-2',6'-Dmt-Lys-Phe-$NH_2$, are demonstrated in U.S. application Ser. No. 11/040,242 (U.S. Pat. No. 7,550,439) and Ser. No. 10/771,232 (U.S. Pat. No. 7,576,061). Accordingly, aromatic-cationic peptides of the present technology, such as D-Arg-2',6'-Dmt-Lys-Phe-$NH_2$, are useful in the prevention and treatment of diseases and conditions caused by, resulting from, or otherwise associated with such cellular events, such as Friedreich's ataxia.

The aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, about nine, or about six.

The amino acids of the aromatic-cationic peptides can be any amino acid. As used herein, the term "amino acid" is used to refer to any organic molecule that contains at least one amino group and at least one carboxyl group. Typically, at least one amino group is at the α position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. Optimally, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta-, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant or insensitive to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, less than four, less than three, or less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is, in some embodiments, a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below is all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 2

| Amino acid number and net positive charges ($3p_m \leq p + 1$) | | | | | | | | | | | | | | | | | | |
|---|---|---|---|---|---|---|---|---|---|---|---|---|---|---|---|---|---|---|
| | (r) | | | | | | | | | | | | | | | | | |
| | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 3

| Amino acid number and net positive charges ($2p_m \le p + 1$) | | | | | | | | | | | | | | | | | | |
|---|---|---|---|---|---|---|---|---|---|---|---|---|---|---|---|---|---|---|
| | (r) | | | | | | | | | | | | | | | | | |
| | 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges or a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 4

| Aromatic groups and net positive charges ($3a \le p_t + 1$ or $a = p_t = 1$) | | | | | | | | | | | | | | | | | | | | |
|---|---|---|---|---|---|---|---|---|---|---|---|---|---|---|---|---|---|---|---|---|
| | ($p_t$) | | | | | | | | | | | | | | | | | | | |
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

TABLE 5

| Aromatic groups and net positive charges ($2a \le p_t + 1$ or $a = p_t = 1$) | | | | | | | | | | | | | | | | | | | | |
|---|---|---|---|---|---|---|---|---|---|---|---|---|---|---|---|---|---|---|---|---|
| | ($p_t$) | | | | | | | | | | | | | | | | | | | |
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

TABLE 6

| EXEMPLARY PEPTIDES |
|---|
| 2',6'-Dmp-D-Arg-2',6'-Dmt-Lys-$NH_2$ |
| 2',6'-Dmp-D-Arg-Phe-Lys-$NH_2$ |
| 2',6'-Dmt-D-Arg-Phe-Orn-$NH_2$ |
| 2',6'-Dmt-D-Arg-Phe-Ahp(2-aminoheptanoicacid)-$NH_2$ |
| 2',6'-Dmt-D-Arg-Phe-Lys-$NH_2$ |
| 2',6'-Dmt-D-Cit-PheLys-$NH_2$ |

TABLE 6-continued

| EXEMPLARY PEPTIDES |
|---|
| Ala-D-Phe-D-Arg-Tyr-Lys-D-Trp-His-D-Tyr-Gly-Phe |
| Arg-D-Leu-D-Tyr-Phe-Lys-Glu-D-Lys-Arg-D-Trp-Lys-D-Phe-Tyr-D-Arg-Gly |

TABLE 6-continued

| EXEMPLARY PEPTIDES |
|---|
| Asp-Arg-D-Phe-Cys-Phe-D-Arg-D-Lys-Tyr-Arg-D-Tyr-Trp-D-His-Tyr-D-Phe-Lys-Phe |
| Asp-D-Trp-Lys-Tyr-D-His-Phe-Arg-D-Gly-Lys-$NH_2$ |
| D-Arg-2',6'-Dmt-Lys-Phe-$NH_2$ |
| D-Glu-Asp-Lys-D-Arg-D-His-Phe-Phe-D-Val-Tyr-Arg-Tyr-D-Tyr-Arg-His-Phe-$NH_2$ |
| D-His-Glu-Lys-Tyr-D-Phe-Arg |
| D-His-Lys-Tyr-D-Phe-Glu-D-Asp-D-Asp-D-His-D-Lys-Arg-Trp-$NH_2$ |
| D-Tyr-Trp-Lys-$NH_2$ |
| Glu-Arg-D-Lys-Tyr-D-Val-Phe-D-His-Trp-Arg-D-Gly-Tyr-Arg-D-Met-$NH_2$ |
| Gly-Ala-Lys-Phe-D-Lys-Glu-Arg-Tyr-His-D-Arg-D-Arg-Asp-Tyr-Trp-D-His-Trp-His-D-Lys-Asp. |
| Gly-D-Phe-Lys-His-D-Arg-Tyr-$NH_2$ |
| His-Tyr-D-Arg-Trp-Lys-Phe-D-Asp-Ala-Arg-Cys-D-Tyr-His-Phe-D-Lys-Tyr-His-Ser-$NH_2$ |
| Lys-D-Arg-Tyr-$NH_2$ |
| Lys-D-Gln-Tyr-Arg-D-Phe-Trp-$NH_2$ |
| Lys-Trp-D-Tyr-Arg-Asn-Phe-Tyr-D-His-$NH_2$ |
| Met-Tyr-D-Arg-Phe-Arg-$NH_2$ |
| Met-Tyr-D-Lys-Phe-Arg |
| Phe-Arg-D-His-Asp |
| Phe-D-Arg-2',6'-Dmt-Lys-$NH_2$ |
| Phe-D-Arg-His |
| Phe-D-Arg-Lys-Trp-Tyr-D-Arg-His |
| Phe-D-Arg-Phe-Lys-$NH_2$ |
| Phe-Phe-D-Tyr-Arg-Glu-Asp-D-Lys-Arg-D-Arg-His-Phe-$NH_2$ |
| Phe-Tyr-Lys-D-Arg-Trp-His-D-Lys-D-Lys-Glu-Arg-D-Tyr-Thr |
| Thr-Gly-Tyr-Arg-D-His-Phe-Trp-D-His-Lys |
| Thr-Tyr-Arg-D-Lys-Trp-Tyr-Glu-Asp-D-Lys-D-Arg-His-Phe-D-Tyr-Gly-Val-Ile-D-His-Arg-Tyr-Lys-$NH_2$ |
| Trp-D-Lys-Tyr-Arg-$NH_2$ |
| Trp-Lys-Phe-D-Asp-Arg-Tyr-D-His-Lys |
| Tyr-Asp-D-Lys-Tyr-Phe-D-Lys-D-Arg-Phe-Pro-D-Tyr-His-Lys |
| Tyr-D-Arg-Phe-Lys-Glu-$NH_2$ |
| Tyr-D-Arg-Phe-Lys-$NH_2$ |
| Tyr-D-His-Phe-D-Arg-Asp-Lys-D-Arg-His-Trp-D-His-Phe |
| Tyr-His-D-Gly-Met |
| Val-D-Lys-His-Tyr-D-Phe-Ser-Tyr-Arg-$NH_2$ |

In one embodiment, the peptides have mu-opioid receptor agonist activity (i.e., they activate the mu-opioid receptor). Peptides, which have mu-opioid receptor agonist activity, are typically those peptides that have a tyrosine residue or a tyrosine derivative at the N-terminus (i.e., the first amino acid position). Suitable derivatives of tyrosine include 2'-methyltyrosine (Mmt); 2',6'-dimethyltyrosine (2',6'-Dmt); 3',5'-dimethyltyrosine (3',5'-Dmt); N,2',6'-trimethyltyrosine (Tmt); and 2'-hydroxy-6'-methyltryosine (Hmt).

In one embodiment, a peptide that has mu-opioid receptor agonist activity has the formula Tyr-D-Arg-Phe-Lys-$NH_2$. Tyr-D-Arg-Phe-Lys-$NH_2$ has a net positive charge of three, contributed by the amino acids tyrosine, arginine, and lysine and has two aromatic groups contributed by the amino acids phenylalanine and tyrosine. The tyrosine of Tyr-D-Arg-Phe-Lys-$NH_2$ can be a modified derivative of tyrosine such as in 2',6'-dimethyltyrosine to produce the compound having the formula 2',6'-Dmt-D-Arg-Phe-Lys-$NH_2$. 2',6'-Dmt-D-Arg-Phe-Lys-$NH_2$ has a molecular weight of 640 and carries a net three positive charge at physiological pH. 2',6'-Dmt-D-Arg-Phe-Lys-$NH_2$ readily penetrates the plasma membrane of several mammalian cell types in an energy-independent manner (Zhao, et al., *J. Pharmacol Exp Ther.,* 304:425-432, 2003).

Alternatively, in other instances, the aromatic-cationic peptide does not have mu-opioid receptor agonist activity. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment. Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N, 2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-$NH_2$. Alternatively, the N-terminal phenylalanine can be a derivative of phenylalanine such as 2',6'-dimethylphenylalanine (2',6'-Dmp). Tyr-D-Arg-Phe-Lys-$NH_2$ containing 2',6'-dimethylphenylalanine at amino acid position 1 has the formula 2',6'-Dmp-D-Arg-Phe-Lys-$NH_2$. In one embodiment, the amino acid sequence of 2',6'-Dmt-D-Arg-Phe-Lys-$NH_2$ is rearranged such that Dint is not at the N-terminus. An example of such an aromatic-cationic peptide that does not have mu-opioid receptor agonist activity has the formula D-Arg-2',6'-Dmt-Lys-Phe-$NH_2$.

Suitable substitution variants of the peptides listed herein include conservative amino acid substitutions. Amino acids may be grouped according to their physicochemical characteristics as follows:

(a) Non-polar amino acids: Ala(A) Ser(S) Thr(T) Pro(P) Gly(G) Cys (C);

(b) Acidic amino acids: Asn(N) Asp(D) Glu(E) Gln(Q);

(c) Basic amino acids: His(H) Arg(R) Lys(K);

(d) Hydrophobic amino acids: Met(M) Leu(L) Ile(I) Val (V); and (e) Aromatic amino acids: Phe(F) Tyr(Y) Trp(W) His (H).

Substitutions of an amino acid in a peptide by another amino acid in the same group are referred to as a conservative substitution and may preserve the physicochemical characteristics of the original peptide. In contrast, substitutions of an amino acid in a peptide by another amino acid in a different group are generally more likely to alter the characteristics of the original peptide.

Examples of peptides that activate mu-opioid receptors include, but are not limited to, the aromatic-cationic peptides shown in Table 7.

TABLE 7

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | $NH_2$ |
| Tyr | D-Arg | Phe | Orn | $NH_2$ |
| Tyr | D-Arg | Phe | Dab | $NH_2$ |
| Tyr | D-Arg | Phe | Dap | $NH_2$ |
| 2'6'Dmt | D-Arg | Phe | Lys | $NH_2$ |
| 2'6'Dmt | D-Arg | Phe | Lys-$NH(CH_2)_2$-NH-dns | $NH_2$ |
| 2'6'Dmt | D-Arg | Phe | Lys-$NH(CH_2)_2$-NH-atn | $NH_2$ |

TABLE 7-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| 2'6'Dmt | D-Arg | Phe | dnsLys | $NH_2$ |
| 2'6'Dmt | D-Cit | Phe | Lys | $NH_2$ |
| 2'6'Dmt | D-Cit | Phe | Ahp | $NH_2$ |
| 2'6'Dmt | D-Arg | Phe | Orn | $NH_2$ |
| 2'6'Dmt | D-Arg | Phe | Dab | $NH_2$ |
| 2'6'Dmt | D-Arg | Phe | Dap | $NH_2$ |
| 2'6'Dmt | D-Arg | Phe | Ahp(2-aminoheptanoic acid) | $NH_2$ |
| Bio-2'6'Dmt | D-Arg | Phe | Lys | $NH_2$ |
| 3'5'Dmt | D-Arg | Phe | Lys | $NH_2$ |
| 3'5'Dmt | D-Arg | Phe | Orn | $NH_2$ |
| 3'5'Dmt | D-Arg | Phe | Dab | $NH_2$ |
| 3'5'Dmt | D-Arg | Phe | Dap | $NH_2$ |
| Tyr | D-Arg | Tyr | Lys | $NH_2$ |
| Tyr | D-Arg | Tyr | Orn | $NH_2$ |
| Tyr | D-Arg | Tyr | Dab | $NH_2$ |
| Tyr | D-Arg | Tyr | Dap | $NH_2$ |
| 2'6'Dmt | D-Arg | Tyr | Lys | $NH_2$ |
| 2'6'Dmt | D-Arg | Tyr | Orn | $NH_2$ |
| 2'6'Dmt | D-Arg | Tyr | Dab | $NH_2$ |
| 2'6'Dmt | D-Arg | Tyr | Dap | $NH_2$ |
| 2'6'Dmt | D-Arg | 2'6'Dmt | Lys | $NH_2$ |
| 2'6'Dmt | D-Arg | 2'6'Dmt | Orn | $NH_2$ |
| 2'6'Dmt | D-Arg | 2'6'Dmt | Dab | $NH_2$ |
| 2'6'Dmt | D-Arg | 2'6'Dmt | Dap | $NH_2$ |
| 3'5'Dmt | D-Arg | 3'5'Dmt | Arg | $NH_2$ |
| 3'5'Dmt | D-Arg | 3'5'Dmt | Lys | $NH_2$ |
| 3'5'Dmt | D-Arg | 3'5'Dmt | Orn | $NH_2$ |
| 3'5'Dmt | D-Arg | 3'5'Dmt | Dab | $NH_2$ |
| Tyr | D-Lys | Phe | Dap | $NH_2$ |
| Tyr | D-Lys | Phe | Arg | $NH_2$ |
| Tyr | D-Lys | Phe | Lys | $NH_2$ |
| Tyr | D-Lys | Phe | Orn | $NH_2$ |
| 2'6'Dmt | D-Lys | Phe | Dab | $NH_2$ |
| 2'6'Dmt | D-Lys | Phe | Dap | $NH_2$ |
| 2'6'Dmt | D-Lys | Phe | Arg | $NH_2$ |
| 2'6'Dmt | D-Lys | Phe | Lys | $NH_2$ |
| 3'5'Dmt | D-Lys | Phe | Orn | $NH_2$ |
| 3'5'Dmt | D-Lys | Phe | Dab | $NH_2$ |
| 3'5'Dmt | D-Lys | Phe | Dap | $NH_2$ |
| 3'5'Dmt | D-Lys | Phe | Arg | $NH_2$ |
| Tyr | D-Lys | Tyr | Lys | $NH_2$ |
| Tyr | D-Lys | Tyr | Orn | $NH_2$ |
| Tyr | D-Lys | Tyr | Dab | $NH_2$ |
| Tyr | D-Lys | Tyr | Dap | $NH_2$ |
| 2'6'Dmt | D-Lys | Tyr | Lys | $NH_2$ |
| 2'6'Dmt | D-Lys | Tyr | Orn | $NH_2$ |
| 2'6'Dmt | D-Lys | Tyr | Dab | $NH_2$ |
| 2'6'Dmt | D-Lys | Tyr | Dap | $NH_2$ |
| 2'6'Dmt | D-Lys | 2'6'Dmt | Lys | $NH_2$ |
| 2'6'Dmt | D-Lys | 2'6'Dmt | Orn | $NH_2$ |
| 2'6'Dmt | D-Lys | 2'6'Dmt | Dab | $NH_2$ |
| 2'6'Dmt | D-Lys | 2'6'Dmt | Dap | $NH_2$ |
| 2'6'Dmt | D-Arg | Phe | dnsDap | $NH_2$ |
| 2'6'Dmt | D-Arg | Phe | atnDap | $NH_2$ |
| 3'5'Dmt | D-Lys | 3'5'Dmt | Lys | $NH_2$ |
| 3'5'Dmt | D-Lys | 3'5'Dmt | Orn | $NH_2$ |
| 3'5'Dmt | D-Lys | 3'5'Dmt | Dab | $NH_2$ |
| 3'5'Dmt | D-Lys | 3'5'Dmt | Dap | $NH_2$ |
| Tyr | D-Lys | Phe | Arg | $NH_2$ |
| Tyr | D-Orn | Phe | Arg | $NH_2$ |
| Tyr | D-Dab | Phe | Arg | $NH_2$ |
| Tyr | D-Dap | Phe | Arg | $NH_2$ |
| 2'6'Dmt | D-Arg | Phe | Arg | $NH_2$ |
| 2'6'Dmt | D-Lys | Phe | Arg | $NH_2$ |
| 2'6'Dmt | D-Orn | Phe | Arg | $NH_2$ |
| 2'6'Dmt | D-Dab | Phe | Arg | $NH_2$ |
| 3'5'Dmt | D-Dap | Phe | Arg | $NH_2$ |
| 3'5'Dmt | D-Arg | Phe | Arg | $NH_2$ |
| 3'5'Dmt | D-Lys | Phe | Arg | $NH_2$ |
| 3'5'Dmt | D-Orn | Phe | Arg | $NH_2$ |
| Tyr | D-Lys | Tyr | Arg | $NH_2$ |

TABLE 7-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Orn | Tyr | Arg | $NH_2$ |
| Tyr | D-Dab | Tyr | Arg | $NH_2$ |
| Tyr | D-Dap | Tyr | Arg | $NH_2$ |
| 2'6'Dmt | D-Arg | 2'6'Dmt | Arg | $NH_2$ |
| 2'6'Dmt | D-Lys | 2'6'Dmt | Arg | $NH_2$ |
| 2'6'Dmt | D-Orn | 2'6'Dmt | Arg | $NH_2$ |
| 2'6'Dmt | D-Dab | 2'6'Dmt | Arg | $NH_2$ |
| 3'5'Dmt | D-Dap | 3'5'Dmt | Arg | $NH_2$ |
| 3'5'Dmt | D-Arg | 3'5'Dmt | Arg | $NH_2$ |
| 3'5'Dmt | D-Lys | 3'5'Dmt | Arg | $NH_2$ |
| 3'5'Dmt | D-Orn | 3'5'Dmt | Arg | $NH_2$ |
| Mmt | D-Arg | Phe | Lys | $NH_2$ |
| Mmt | D-Arg | Phe | Orn | $NH_2$ |
| Mmt | D-Arg | Phe | Dab | $NH_2$ |
| Mmt | D-Arg | Phe | Dap | $NH_2$ |
| Tmt | D-Arg | Phe | Lys | $NH_2$ |
| Tmt | D-Arg | Phe | Orn | $NH_2$ |
| Tmt | D-Arg | Phe | Dab | $NH_2$ |
| Tmt | D-Arg | Phe | Dap | $NH_2$ |
| Hmt | D-Arg | Phe | Lys | $NH_2$ |
| Hmt | D-Arg | Phe | Orn | $NH_2$ |
| Hmt | D-Arg | Phe | Dab | $NH_2$ |
| Hmt | D-Arg | Phe | Dap | $NH_2$ |
| Mmt | D-Lys | Phe | Lys | $NH_2$ |
| Mmt | D-Lys | Phe | Orn | $NH_2$ |
| Mmt | D-Lys | Phe | Dab | $NH_2$ |
| Mmt | D-Lys | Phe | Dap | $NH_2$ |
| Mmt | D-Lys | Phe | Arg | $NH_2$ |
| Tmt | D-Lys | Phe | Lys | $NH_2$ |
| Tmt | D-Lys | Phe | Orn | $NH_2$ |
| Tmt | D-Lys | Phe | Dab | $NH_2$ |
| Tmt | D-Lys | Phe | Dap | $NH_2$ |
| Tmt | D-Lys | Phe | Arg | $NH_2$ |
| Hmt | D-Lys | Phe | Lys | $NH_2$ |
| Hmt | D-Lys | Phe | Orn | $NH_2$ |
| Hmt | D-Lys | Phe | Dab | $NH_2$ |
| Hmt | D-Lys | Phe | Dap | $NH_2$ |
| Hmt | D-Lys | Phe | Arg | $NH_2$ |
| Mmt | D-Lys | Phe | Arg | $NH_2$ |
| Mmt | D-Orn | Phe | Arg | $NH_2$ |
| Mmt | D-Dab | Phe | Arg | $NH_2$ |
| Mmt | D-Dap | Phe | Arg | $NH_2$ |
| Mmt | D-Arg | Phe | Arg | $NH_2$ |
| Tmt | D-Lys | Phe | Arg | $NH_2$ |
| Tmt | D-Orn | Phe | Arg | $NH_2$ |
| Tmt | D-Dab | Phe | Arg | $NH_2$ |
| Tmt | D-Dap | Phe | Arg | $NH_2$ |
| Tmt | D-Arg | Phe | Arg | $NH_2$ |
| Hmt | D-Lys | Phe | Arg | $NH_2$ |
| Hmt | D-Orn | Phe | Arg | $NH_2$ |
| Hmt | D-Dab | Phe | Arg | $NH_2$ |
| Hmt | D-Dap | Phe | Arg | $NH_2$ |
| Hmt | D-Arg | Phe | Arg | $NH_2$ |

Dab = diaminobutyric
Dap = diaminopropionic acid
Dmt = dimethyltyrosine
Mmt = 2'-methyltyrosine
Tmt = N, 2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of peptides that do not activate mu-opioid receptors include, but are not limited to, the aromatic-cationic peptides shown in Table 8.

TABLE 8

| Peptide Analogs Lacking Mu-Opioid Activity | | | | |
|---|---|---|---|---|
| Amino Acid Position 1 | Amino Acid Position 2 | Amino Acid Position 3 | Amino Acid Position 4 | C-Terminal Modification |
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Phe | Lys | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexyl alanine

The amino acids of the peptides shown in Table 5 and 6 may be in either the L- or the D-configuration.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.,* 289, Academic Press, Inc., New York (1997).

Friedreich's Ataxia

Friedreich's ataxia is an inherited autosomal recessive disease that causes progressive damage to the nervous system. The ataxia results from the degeneration of nerve tissue in the spinal cord, in particular, sensory neurons essential for directing muscle movement of the arms and legs. The spinal cord becomes thinner and nerve cells lose some of their myelin sheath.

Symptoms typically begin between the ages of 5 and 15 years, although they sometimes appear in adulthood. The first symptom to appear is usually gait ataxia, or difficulty walking. The ataxia gradually worsens and slowly spreads to the arms and the trunk. There is often loss of sensation in the extremities, which may spread to other parts of the body. Other features include loss of tendon reflexes, especially in the knees and ankles. Most people with Friedreich's ataxia develop scoliosis, which often requires surgical intervention for treatment. Dysarthria (slowness and slurring of speech) develops and can get progressively worse. Many individuals with later stages of Friedreich's ataxia develop hearing and vision loss.

Heart disease often accompanies Friedreich's ataxia, such as hypertrophic cardiomyopathy (enlargement of the heart), myocardial fibrosis (formation of fiber-like material in the muscles of the heart), and cardiac failure. Heart rhythm abnormalities such as tachycardia (fast heart rate) and heart block (impaired conduction of cardiac impulses within the heart) are also common. Other symptoms that may occur include chest pain, shortness of breath, and heart palpitations.

About 20 percent of people with Friedreich's ataxia develop carbohydrate intolerance and 10 percent develop diabetes. Most individuals with Friedreich's ataxia tire very easily and find that they require more rest and take a longer time to recover from common illnesses such as colds and flu.

The rate of progression varies from person to person. Generally, within 10 to 20 years after the appearance of the first symptoms, the person is confined to a wheelchair, and in later stages of the disease individuals may become completely incapacitated. Friedreich's ataxia can shorten life expectancy, and heart disease is the most common cause of death.

Friedreich's ataxia occurs when a mutated FXN gene contains amplified intronic GAA repeats. The mutant FXN gene contains expanded GAA triplet repeats in the first intron; in a few pedigrees, point mutations have been detected. Since the defect is located in an intron, which is removed from the mRNA transcript between transcription and translation, the mutated FXN gene does not result in the production of abnormal proteins. Instead, the mutation causes gene silencing, i.e., the mutation decreases the transcription of the gene, through induction of a heterochromatin structure in a manner similar to position-effect variegation. The GAA repeat expansion in FXN and subsequent gene silencing results in the reduction of frataxin levels.

The FXN gene encodes the protein frataxin. Frataxin is a highly conserved iron binding protein. Human frataxin is synthesized as a 210 amino acid precursor that is imported to the mitochondria via the mitochondrial targeting signal contained in the N-terminus. The frataxin precursor is subsequently cleaved to a mature 14 kDa protein (residues 81-210).

Frataxin binds both $Fe^{2+}$ and $Fe^{3+}$ ions in an electrostatic manner and functions as an iron chaperone during Fe—S cluster assembly. Frataxin directly binds to the central Fe—S cluster assembly complex, which is composed of Nfs1 enzyme and Isu scaffold protein. Nfs1 is a cysteine desulfurase used in the synthesis of sulfur bioorganic derivatives and Isu is the transient scaffold protein on which the Fe—S cluster assembles. Frataxin increases the efficiency of Fe—S cluster formation, which is required to activate the mitochondrial Kreb cycle enzyme aconitase. Frataxin also plays a role in mitochondrial iron storage and heme biosynthesis by incorporating mitochondrial iron into protoporphyrin (PIX).

Loss of frataxin function results in the disruption of iron-sulfur cluster biosynthesis, mitochondrial iron overload, oxidative stress, impaired aerobic electron transport chain respiration and cell death in the brain, spinal cord and heart. Studies have also shown that frataxin protects dopaminergic neuronal cells against MPTP-induced toxicity in a mouse model of Parkinson's disease.

Mitochondrial iron overload leads to impaired intra-mitochondrial metabolism and a defective mitochondrial respiratory chain. A defective mitochondrial respiratory chain leads to increased free radical generation and oxidative damage, which may be considered as mechanisms that compromise cell viability. Recent evidence suggests that frataxin might detoxify reactive oxygen species (ROS) via activation of glutathione peroxidase and elevation of thiols. (See e.g., Calabrese et al., *Journal of the Neurological Sciences,* 233(1): 145-162 (June 2005)).

In some embodiments, treatment with an aromatic-cationic peptide, such as D-Arg-2',6'-Dmt-Lys-Phe-$NH_2$, or a pharmaceutically acceptable salt thereof, such as acetate or trifluoroacetate salt, stabilizes the mitochondrial metabolism in a tissue or an organ in mammalian subjects that have suffered or are at risk of suffering Friedreich's ataxia. By way of example, but not by way of limitation, in some embodiments, mitochondrial metabolism is increased in the spinal cord of a treated subject.

In some embodiments, treatment with an aromatic-cationic peptide, such as D-Arg-2',6'-Dmt-Lys-Phe-$NH_2$, or a pharmaceutically acceptable salt thereof, such as acetate or trifluoroacetate salt, reduces free radical generation, oxidative stress, or both in a tissue or an organ in mammalian subjects that have suffered or are at risk of suffering Friedreich's ataxia. By way of example, but not by way of limitation, in some embodiments, free radical generation, oxidative damage, or both are increased in the spinal cord of a treated subject.

In some embodiments, treatment with an aromatic-cationic peptide, such as D-Arg-2',6'-Dmt-Lys-Phe-$NH_2$, or a pharmaceutically acceptable salt thereof, such as acetate or trifluoroacetate salt, reduces build-up of iron in the mitochondria in a tissue or an organ in mammalian subjects that have suffered or are at risk of suffering Friedreich's ataxia. By way of example, but not by way of limitation, in some embodiments, iron in the mitochondria decreases in the spinal cord of a treated subject.

Therapeutic Methods

The following discussion is presented by way of example only, and is not intended to be limiting.

One aspect of the present technology includes methods of treating reduced frataxin expression in a subject diagnosed as having, suspected as having, or at risk of having reduced frataxin expression levels. One aspect of the present technology includes methods of treating Friedreich's ataxia in a subject diagnosed as having, suspected as having, or at risk of having Friedreich's ataxia. In therapeutic applications, compositions or medicaments comprising an aromatic-cationic peptide such as D-Arg-2',6'-Dmt-Lys-Phe-$NH_2$, or a pharmaceutically acceptable salt thereof, such as acetate or trifluoroacetate salt, are administered to a subject suspected of, or already suffering from such a disease, such as, e.g., decreased frataxin expression levels or Friedreich's ataxia, in an amount sufficient to reduce the severity at least partially arrest or delay the onset of one or more of the symptoms of the disease, including its complications and intermediate pathological phenotypes in development of the disease.

Subjects suffering from decreased frataxin expression levels or Friedreich's ataxia can be identified by any or a combination of diagnostic or prognostic assays known in the art. For example, typical symptoms of Friedreich's ataxia include symptoms such as, e.g., muscle weakness, especially in the arms and legs, loss of coordination, motor control impairment, vision impairment, hearing impairment, slurred speech, curvature of the spine, diabetes, and heart disorders. In some embodiments, the subject may exhibit reduced levels of frataxin expression compared to a normal subject, which are measureable using techniques known in the art. In some embodiments, the subject may exhibit one or more mutations in the FXN gene associated with Friedreich's ataxia, which are detectable using techniques known in the art.

Prophylactic Methods

In one aspect, the present technology provides a method for preventing or delaying the onset of Friedreich's ataxia or symptoms of Friedreich's ataxia in a subject at risk of having reduced levels of frataxin expression compared to a normal subject. In some embodiments, the subject may exhibit one or more mutations in the FXN gene associated with Friedreich's ataxia, which are detectable using techniques known in the art. Subjects at risk for reduced frataxin expression levels or Friedreich's ataxia can be identified by, e.g., any or a combination of diagnostic or prognostic assays known in the art. In prophylactic applications, pharmaceutical compositions or medicaments of aromatic-cationic peptides, such as D-Arg-2',6'-Dmt-Lys-Phe-$NH_2$, or a pharmaceutically acceptable salt thereof, such as acetate or trifluoroacetate salt, are administered to a subject susceptible to, or otherwise at risk of a disease or condition such as e.g., Friedreich's ataxia, in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Administration of a prophylactic aromatic-cationic can occur prior to the manifestation of symptoms characteristic of the disease or disorder, such that the disease or disorder is prevented or, alternatively, delayed in its progression.

Subjects or at risk for reduced frataxin expression levels or Friedreich's ataxia may exhibit one or more of the following non-limiting risk factors: cardiomyopathy, skeletal muscle abnormalities, neutropenia, slow development, weak muscle tone, increased levels of organic acids in the urine and blood, and/or frequent bacterial infections, such as pneumonia.

For therapeutic and/or prophylactic applications, a composition comprising an aromatic-cationic peptide, such as D-Arg-2',6'-Dmt-Lys-Phe-$NH_2$, or a pharmaceutically acceptable salt thereof, such as acetate or trifluoroacetate salt, is administered to the subject. In some embodiments, the peptide composition is administered one, two, three, four, or five times per day. In some embodiments, the peptide composition is administered more than five times per day. Additionally or alternatively, in some embodiments, the peptide composition is administered every day, every other day, every third day, every fourth day, every fifth day, or every sixth day. In some embodiments, the peptide composition is administered weekly, bi-weekly, tri-weekly, or monthly. In some embodiments, the peptide composition is administered for a period of one, two, three, four, or five weeks. In some embodiments, the peptide is administered for six weeks or more. In some embodiments, the peptide is administered for twelve weeks or more. In some embodiments, the peptide is administered for a period of less than one year. In some embodiments, the peptide is administered for a period of more than one year.

For therapeutic and/or prophylactic applications, a composition comprising an aromatic-cationic peptide, such as D-Arg-2',6'-Dmt-Lys-Phe-$NH_2$, or a pharmaceutically acceptable salt thereof, such as acetate or trifluoroacetate salt, may be administered in combination with one or more additional agents. In some embodiments, there is a synergistic effect between the peptide and the one or more additional agents.

Determination of the Biological Effect of the Aromatic-Cationic Peptide-Based Therapeutic In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect increasing frataxin expression, and preventing or treating Friedreich's ataxia. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of D-Arg-2',6'-Dmt-Lys-Phe-$NH_2$, or a pharmaceutically acceptable salt thereof, such as acetate or trifluoroacetate salt.

Modes of Administration and Effective Dosages

Any method known to those in the art for contacting a cell, organ or tissue with an aromatic-cationic peptide of the present technology, such as D-Arg-2',6'-Dmt-Lys-Phe-$NH_2$, or a pharmaceutically acceptable salt thereof, such as acetate or trifluoroacetate salt, may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides, such as D-Arg-2',6'-Dmt-Lys-Phe-$NH_2$, or a pharmaceutically acceptable salt thereof, such as acetate or trifluoroacetate salt, are administered to the subject in effective amounts (i.e., amounts that have desired therapeutic effect). The dose and dosage regimen will depend upon the degree of the disease in the subject, the characteristics of the particular aromatic-cationic peptide used, e.g., its therapeutic index, the subject, and the subject's history.

The effective amount may be determined during pre-clinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid, which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate or trifluoroacetate salt.

The aromatic-cationic peptides described herein, such as D-Arg-2',6'-Dmt-Lys-Phe-$NH_2$, or a pharmaceutically acceptable salt thereof, such as acetate or trifluoroacetate salt, can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomersal, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed my iontophoresis.

A therapeutic protein or peptide can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. s one skilled in the art would appreciate, there are a variety of methods to prepare liposomes. (See Lichtenberg, et al., *Methods Biochem. Anal.,* 33:337-462 (1988); Anselem, et al., *Liposome Technology*, CRC Press (1993)). Liposomal formulations can delay clearance and increase cellular uptake (See Reddy, *Ann. Pharmacother.,* 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.,* 34(7-8):915-923 (2000)). A polymer formulation for human growth hormone (hGH) has been used in clinical trials. (See Kozarich and Rich, *Chemical Biology,* 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi, et al., *Cancer Lett.*, 100: 63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies, in some embodiments, within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.001-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and in some embodiments, until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, and in some embodiments, by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In a preferred embodiment, the mammal is a human.

Combination Therapy with an Aromatic-Cationic Peptide and Other Therapeutic Agents In some embodiments, one or more additional therapeutic agents are administered to a subject in combination with an aromatic-cationic peptide, e.g., D-Arg-2',6'-Dmt-Lys-Phe-$NH_2$, or a pharmaceutically acceptable salt thereof, such as acetate or trifluoroacetate salt, such that a synergistic therapeutic effect is produced. A "synergistic therapeutic effect" refers to a greater-than-additive therapeutic effect, which is produced by a combination of at least two therapeutic agents, and which exceeds that which would otherwise result from administration of any individual therapeutic agent alone. Therefore, lower doses of one or more of any individual therapeutic agent may be used in treating a medical disease or condition, e.g., disruptions in mitochondrial oxidative phosphorylation, resulting in increased therapeutic efficacy and decreased side-effects. By way of example, but not by way of limitation, exemplary additional therapeutic agents that can be combined with aromatic-cationic peptides for the treatment or prevention of Friedreich's ataxia include, but are not limited to, ACE inhibitors, e.g., digoxin, enalapril, or lisinopril, diuretics, beta-blockers, idebenone, deferiprone, and insulin.

The multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

EXAMPLES

The present compositions and methods are further illustrated by the following examples, which should not be construed as limiting in any way.

Example 1: Aromatic-Cationic Peptides Rescue Friedreich's Ataxia Fibroblasts from Iron-Oxidant Stress This example demonstrates the effect of the aromatic-cationic peptide D-Arg-2',6'-Dmt-Lys-Phe-$NH_2$ on fibroblasts from Friedreich's ataxia (FRDA) patients that have induced iron-oxidant stress.

Methods: In the absence of FXN, it is widely accepted that deficient cells will have an increased sensitivity to oxidative stress, which most likely contributes to the cascade of events leading to cytotoxicity. Iron with hydroquinone (HQ) induces oxidative stress in cells because HQ forms a lipophilic chelate with iron and rapidly transfers the metal across the normally impermeable plasma membrane. HQ or Fe alone in culture media is not toxic to FRDA fibroblasts even after an extended exposure of 24 hours.

FRDA fibroblasts are treated with 1-10 μM D-Arg-2',6'-Dmt-Lys-Phe-$NH_2$ in culture media for 24 hours. After 24 hours, the media is changed and the cells are treated with 5 μm Fe/HQ for 5 hours. Controls include FRDA fibroblasts without D-Arg-2',6'-Dmt-Lys-Phe-$NH_2$ and then treated with 5 μm Fe/HQ for 5 hours and FRDA fibroblasts treated with D-Arg-2',6'-Dmt-Lys-Phe-$NH_2$ for 24 hours and no addition of Fe/HQ.

Results: It is anticipated that cells that are treated only with Fc/HQ will show changes in the morphology and have loss of adherence, which indicates that Fe/HQ is cytotoxic. It is anticipated that cells that were treated with D-Arg-2',6'-Dmt-Lys-Phe-$NH_2$ prior to the addition of Fe/HQ will be able to survive and show reduced evidence of cytotoxicity as demonstrated by their morphologic appearance being substantially identical to, or less deformed than cells treated only with D-Arg-2',6'-Dmt-Lys-Phe-$NH_2$.

These results will show that aromatic-cationic peptides of the present disclosure, such as D-Arg-2',6'-Dmt-Lys-Phe-$NH_2$, or a pharmaceutically acceptable salt thereof, such as acetate or trifluoroacetate salt, are useful in the prevention and treatment of diseases and conditions associated with reduced frataxin expression levels. It is further expected that administration of D-Arg-2',6'-Dmt-Lys-Phe-$NH_2$ in combination with one or more additional therapeutic agents will have synergistic effects in this regard. It is further anticipated that these results will show that aromatic-cationic peptides of the present disclosure, such as D-Arg-2',6'-Dmt-Lys-Phe-$NH_2$, or a pharmaceutically acceptable salt thereof, such as acetate or trifluoroacetate salt, are useful in methods comprising administration of the peptide to subjects having or susceptible to Friedreich's ataxia.

Example 2: Aromatic-Cationic Peptides Prolong Survival of FXN-Knockout Mice

This example demonstrates the effect of the aromatic-cationic peptide D-Arg-2',6'-Dmt-Lys-Phe-$NH_2$ on survival of FXN-knockout (KO) mice.

Methods: FXN-KO mice are treated with 1-10 μM D-Arg-2',6'-Dmt-Lys-Phe-$NH_2$ or PBS beginning at Day 3 of life for 60 days. The mice receive the aromatic peptide and PBS by intraperitoneal (IP) injections three times per week. All mice will need to reach an age of 10 days to be included in the study, and all mice will be weaned at 28 days of age. Control animals include of littermates heterozygous for the conditional allele and had no clinical or biochemical phenotype. The control heterozygous littermates receive equivalent volume injections of PBS.

Results: It is anticipated that FXN-KO mice treated with D-Arg-2',6'-Dmt-Lys-Phe-$NH_2$ will have increased survival as compared to FXN-KO mice treated with PBS. It is further expected that administration of D-Arg-2',6'-Dmt-Lys-Phe-$NH_2$ in combination with one or more additional therapeutic agents will have synergistic effects in this regard.

These results will show that aromatic-cationic peptides of the present disclosure, such as D-Arg-2',6'-Dmt-Lys-Phe-$NH_2$, or a pharmaceutically acceptable salt thereof, such as acetate or trifluoroacetate salt, are useful in the prevention and treatment of Friedreich's ataxia.

Example 3: Use of Aromatic-Cationic Peptides in the Treatment of Friedreich's Ataxia This example will demonstrate the use of aromatic-cationic peptides, such as D-Arg-2',6'-Dmt-Lys-Phe-$NH_2$, or a pharmaceutically acceptable salt thereof, such as acetate or trifluoroacetate salt, in the treatment of Friedreich's ataxia.

Methods: Friedreich's ataxia patients receive daily administrations of a therapeutically effective (e.g., 1-10 mg/kg body weight) amount of aromatic-cationic peptide, such as D-Arg-2',6'-Dmt-Lys-Phe-$NH_2$, or a pharmaceutically acceptable salt thereof, such as acetate or trifluoroacetate salt. Peptides may be administered orally, topically, systemically, intravenously, subcutaneously, intraperitoneally, or intramuscularly according to methods known in the art. Subjects are evaluated weekly for the presence and/or severity of signs and symptoms associated with Friedreich's ataxia, including, but not limited to, e.g., muscle weakness, especially in the arms and legs, loss of coordination, motor control impairment, vision impairment, hearing impairment, slurred speech, curvature of the spine, diabetes, and heart disorders. Treatments are maintained until such a time as symptoms of Friedreich's ataxia are ameliorated or eliminated.

Results: It is predicted that Friedreich's ataxia subjects receiving therapeutically effective amounts of aromatic-cationic peptide, such as D-Arg-2',6'-Dmt-Lys-Phe-$NH_2$, or a pharmaceutically acceptable salt thereof, such as acetate or trifluoroacetate salt will display reduced severity of symptoms associated with Friedreich's ataxia. It is further expected that administration of D-Arg-2',6'-Dmt-Lys-Phe-$NH_2$ in combination with one or more additional therapeutic agents will have synergistic effects in this regard.

These results will show that aromatic-cationic peptides, such as D-Arg-2',6'-Dmt-Lys-Phe-$NH_2$, or a pharmaceutically acceptable salt thereof, such as acetate or trifluoroacetate salt are useful in the treatment of Friedreich's ataxia. Accordingly, the peptides are useful in methods comprising administering aromatic-cationic peptides to a subject in need thereof for the treatment of Friedreich's ataxia.

Example 4: Use of Aromatic-Cationic Peptides in Combination with Other Agents to Reduce Symptoms of Friedreich's Ataxia This example will demonstrate the synergetic effect from the use of aromatic-cationic peptides, such as D-Arg-2',6'-

Dmt-Lys-Phe-$NH_2$, or a pharmaceutically acceptable salt thereof, such as acetate or trifluoroacetate salt, and another agent, e.g., idebenone, in the treatment of Friedreich's ataxia.

Methods: Friedreich's ataxia patients are split into four groups. Group 1 receives daily administrations of a therapeutically effective amount of aromatic-cationic peptide (e.g., 1-10 mg/kg body weight), such as D-Arg-2',6'-Dmt-Lys-Phe-$NH_2$, or a pharmaceutically acceptable salt thereof, such as acetate or trifluoroacetate salt. Peptides may be administered orally, topically, systemically, intravenously, subcutaneously, intraperitoneally, or intramuscularly according to methods known in the art.

Group 2 receives daily administrations of a therapeutically effective amount of a known agent used in the treatment of Friedreich's ataxia, e.g., 100 mg idebenone. The known agent may be administered orally, topically, systemically, intravenously, subcutaneously, intraperitoneally, or intramuscularly according to methods known in the art.

Group 3 receives daily administrations of D-Arg-2',6'-Dmt-Lys-Phe-$NH_2$ and the same agent as Group 2, wherein the dosage of D-Arg-2',6'-Dmt-Lys-Phe-$NH_2$ and the agent is the same amount used in Groups 1 and 2, respectively. D-Arg-2',6'-Dmt-Lys-Phe-$NH_2$ and the known agent may be administered orally, topically, systemically, intravenously, subcutaneously, intraperitoneally, or intramuscularly according to methods known in the art. D-Arg-2',6'-Dmt-Lys-Phe-$NH_2$ and the agent may be administered simultaneously, either as a single pill or as two separate pills, in any order or not simultaneously, e.g., idebenone is given an hour after treatment with D-Arg-2',6'-Dmt-Lys-Phe-$NH_2$.

The fourth groups receives a similar treatment as Group 3, except at half the dosage of both D-Arg-2',6'-Dmt-Lys-Phe-$NH_2$ and the known agent.

Subjects are evaluated weekly for the presence and/or severity of signs and symptoms associated with Friedreich's ataxia, including, but not limited to, e.g., muscle weakness, especially in the arms and legs, loss of coordination, motor control impairment, vision impairment, hearing impairment, slurred speech, curvature of the spine, diabetes, and heart disorders. Treatments are maintained until such a time as symptoms of Friedreich's ataxia are ameliorated or eliminated.

Results: It is predicted that Groups 1 and 2 will display reduced severity of symptoms associated with Friedreich's ataxia. It is predicted that Group 3 will show a greater reduction in the severity of symptoms or elimination of symptoms associated with Friedreich's ataxia. It is predicted that Group 4 will displayed reduced severity of symptoms associated with Friedreich's ataxia equal to or great than the reduction of symptoms in Groups 1 and 2.

These results will show that the combination of aromatic-cationic peptides, such as D-Arg-2',6'-Dmt-Lys-Phe-$NH_2$, or a pharmaceutically acceptable salt thereof, such as acetate or trifluoroacetate salt, and known agents used to treat Friedreich's ataxia are useful in the treatment of Friedreich's ataxia. The synergistic effect of the combination of the two treatments can lead to a reduced dosage of both compounds, thereby reducing possible side effects of the compounds. Accordingly, the peptides are useful in methods comprising administering aromatic-cationic peptides to a subject in need thereof for the treatment of Friedreich's ataxia.

Example 5: Treatment of Friedreich's Ataxia Using D-Arg-2',6'-Dmt-Lys-Phe-$NH_2$ This example will demonstrate the use of aromatic-cationic peptides, such as D-Arg-2',6'-Dmt-Lys-Phe-$NH_2$, or a pharmaceutically acceptable salt thereof, such as acetate or trifluoroacetate salt, in the treatment of Friedreich's ataxia.

Methods: 24 subjects diagnosed with Friedreich's ataxia are randomly split into four groups (3 test groups and 1 control group) with six subjects per group. Group 1 receives daily intravenous administrations of D-Arg-2',6'-Dmt-Lys-Phe-$NH_2$ at 0.1 mg/kg of body weight. Group 2 receives daily intravenous administrations of D-Arg-2',6'-Dmt-Lys-Phe-$NH_2$ at 0.5 mg/kg of body weight. Group 3 receives daily intravenous administrations of D-Arg-2',6'-Dmt-Lys-Phe-$NH_2$ at 1.0 mg/kg of body weight. Group 4 receives daily intravenous administrations of a control peptide at 1.0 mg/kg of body weight.

Subjects are selected based on: 1) having a molecular genetic diagnosis of Friedreich's ataxia (FRDA) consisting of a GAA-repeat expansion on both alleles of the FXN gene; 2) FRDA patients over the age of 18 years; 3) subjects must be well enough and willing to provide written informed consent; and 4) a female subject is eligible to participate if she is of: a) non-childbearing potential defined as premenopausal females with a documented tubal ligation or hysterectomy; or postmenopausal defined as 12 months of spontaneous amenorrhea (in questionable cases a blood sample with simultaneous follicle stimulating hormone (FSH) >40 MIU/ml and estradiol <40 pg/ml (<140 pmol/L) is confirmatory); b) child-bearing potential and agrees to use one of the following contraception methods: abstinence, contraceptive methods with a failure rate of <1%, oral contraceptive (either combined or progestogen alone), injectable progestogen, implants of levonorgestrel, estrogenic vaginal ring, percutaneous contraceptive patches, intrauterine device (IUD) or intrauterine system (IUS) that meets the <1% failure rate as stated in the product label, male partner(s) sterilization (vasectomy with documentation of azoospermia) prior to the female subject's entry into the study, double barrier method, e.g., condom and occlusive cap (diaphragm or cervical/vault caps) plus vaginal spermicidal agent (foam/gel/film/cream/suppository).

FRDA subjects are excluded based on: 1) subjects with significant clinical dysphagia; 2) subjects taking sodium valproate or any other known histone deacetylase inhibitor; 3) subject's participating in another clinical trial or who have done so within 30 days before screening; 4) subjects known to be positive for human immunodeficiency virus (HIV); 5) subjects with any additional medical condition or illness that, in the opinion of the investigator would interfere with study compliance and/or impair the patient's ability to participate or complete the study; 6) concurrent diseases or conditions that may interfere with study participation or safety include liver disease, bleeding disorders, arrhythmias, organ transplant, organ failure, current neoplasm, poorly controlled diabetes mellitus, poorly controlled hypertension, clinically significant haematological or biochemical abnormality; 7) subjects with a history of substance abuse (e.g., alcohol or drug abuse) within the previous 6 months before enrollment; 8) subjects with a history of severe allergies; 9) inability to provide informed consent; 10) female subjects who are lactating or pregnant (positive pre-randomisation serum pregnancy test) or plan to become pregnant during the study; and 11) subjects unable or unwilling to provide written informed consent Subjects are evaluated every two weeks for the presence and/or severity of signs and symptoms associated with Friedreich's ataxia, which including, but are not limited to, e.g., muscle weakness, loss of coordination, motor control impairment, vision impairment, hearing impairment, slurred speech, curvature of the spine, diabetes, and heart disorders. Treatments and evaluations are maintained for 12 months.

Methods for measuring loss of coordination include, but are not limited to, Functional Reach Test, Pediatric Clinical Test of Sensory Interaction for Balance, the Pediatric Balance Scale, the Timed "Up & Go" Test, the Timed "Up and Down Stairs" Test, and the measurement of static standing.

Methods for measuring loss of coordination include, but are not limited to, force control measurements of various muscle groups using dynamometer in the isometric testing mode.

Results: It is anticipated that Groups 1, 2, and 3 will display reduced severity of symptoms associated with Friedreich's ataxia as compared to Group 4. It is also anticipated that Groups 1, 2, and 3 will show a dose dependent reduction in the severity of symptoms associated with Friedreich's ataxia.

These results will show that the combination of aromatic-cationic peptides, such as D-Arg-2',6'-Dmt-Lys-Phe-$NH_2$, or a pharmaceutically acceptable salt thereof, such as acetate or trifluoroacetate salt, and known agents used to treat Friedreich's ataxia are useful in the treatment of Friedreich's ataxia. The synergistic effect of the combination of the two treatments can lead to a reduced dosage of both compounds, thereby reducing possible side effects of the compounds. Accordingly, the peptides are useful in methods comprising administering aromatic-cationic peptides to a subject in need thereof for the treatment of Friedreich's ataxia.

Example 6: Aromatic-Cationic Peptides Restore Mitochondrial Membrane Potential and Translocation of Frataxin into Mitochondria This example will demonstrate that aromatic-cationic peptides, such as D-Arg-2',6'-Dmt-Lys-Phe-$NH_2$, or a pharmaceutically acceptable salt thereof, such as acetate or trifluoroacetate salt, restore mitochondrial membrane potential and increase translocation of frataxin into the mitochondria.

Methods and Materials

Cell line: P131 is a lymphoblast cell line with deficient frataxin expression. P131 is transfected with a pcDFRDAHA1 vector that contains the 210 amino acid human frataxin tagged with a HA1 epitope. The transcriptional unit is under the control of the CMV immediate-early promoter. The plasmid also encodes the geneticin resistance gene for selection of transfectants. The inserted sequence is confirmed by DNA sequencing. Plasmid DNA is prepared using a DNA miniprep commercial kit (Promega, Madison, Wis.). DNA quality is determined by restriction endonuclease digestion and quantified by UV spectrophotometry.

Transfected lymphoblast line P131 is prepared by growing P131 in fresh medium for 16 hours, and then transiently transfecting P131 with 2 μg/ml pcDFRDAHA1 expression vector or pcDFRDAHA1 empty vector, or 1 μg/ml of the reporter gene plasmid pCMV.sport-βgal using DMRIE-C (Life-Tech, CA) according to the manufacturer's protocol for suspension cells. Each transfection is performed in triplicate in 6-well plates with 2 μg of plasmid DNA, 6 μl of DMRIE-C and $2\times10^6$ cells mixed in 1.2 ml/well of OPTI-MEM low-serum medium. Five hours after transfection, fresh culture medium is added.

24 hours after transfection, cells are stained with X-gal to determine transfection efficiency and selected with 400 μg/ml geneticin for 12 days. Frataxin gene expression is examined by semiquantitative and quantitative RT-PCR and anchored-RT-PCR, western blot and dot blot as described below. Cell lines expressing low (i.e., having similar frataxin expression levels as cells from a subject diagnosed with Friedreich's ataxia), and high frataxin levels are selected for assays, and aliquots of cells are frozen for experiments. Frataxin mRNA expression levels are periodically examined by quantitative RT-PCR on the lightcycler.

Measuring Mitochondrial Potential: Transfected P131 cells are plated on a dish and treated with 0.1 mM t-butyl hydroperoxide (t-BHP), alone or with 1 nM D-Arg-2',6'-Dmt-Lys-Phe-$NH_2$, for 6 hours. Cell untreated with t-BHP and D-Arg-2',6'-Dmt-Lys-Phe-$NH_2$ are used as a control. Cells are then treated with 10 μm of dichlorofluorescin (ex/em=485/530) for 30 minutes at 37° C., 5% $CO_2$. The cells are subjected to a wash with HBSS three time and stained with 20 nM of Mitotracker TMRM (ex/em=550/575 nm) for 15 minutes at 37° C. The cells are then examined by confocal laser scanning microscopy.

Measuring Translocation of Frataxin: Transfected P131 cells that exhibit low or high expression of frataxin are plated onto six dishes, wherein three dishes are treated with 1 nM D-Arg-2',6'-Dmt-Lys-Phe-$NH_2$ and three dishes are not treated, i.e., control cells. After 6 hours, each dish is washed with wash buffer and fix for staining. Frataxin is fluorescently tagged by treating the cells with FITC anti-HA1 antibodies for about one hour at room temperature. Each plate is then examined by fluorescence microscope (Axiovert™) Transfected P131 cells that exhibit low expression of frataxin mimic the disease state of Friedreich's ataxia. A parallel assay using transfected P131 cells that exhibit high expression of frataxin is performed.

Results

It is anticipated that t-BHP treated transfected P131 cells without D-Arg-2',6'-Dmt-Lys-Phe-$NH_2$ treatment will show a loss of TMRM fluorescence, which indicates mitochondrial depolarization. It is anticipated that t-BHP treated transfected P131 cells with D-Arg-2',6'-Dmt-Lys-Phe-$NH_2$ treatment will show TMRM fluorescence, which indicates prevention of mitochondrial depolarization and restoration of the membrane potential. It is anticipated that cell not treated with either t-BHP or D-Arg-2',6'-Dmt-Lys-Phe-$NH_2$ will also show a loss of TMRM fluorescence, however the loss will be less than the t-BHP only treated cells.

It is anticipated that transfected P131 cells that exhibit low and high frataxin expression level when treated with D-Arg-2',6'-Dmt-Lys-Phe-$NH_2$ will show an increase in frataxin localized to the inner membrane of the mitochondria as compared to transfected P131 cells not treated with D-Arg-2',6'-Dmt-Lys-Phe-$NH_2$.

These results will show that D-Arg-2',6'-Dmt-Lys-Phe-$NH_2$ is useful for restoring mitochondrial membrane potential. The results will also show that maintaining the mitochondrial membrane potential results in the translocation of frataxin to the inner mitochondrial membrane.

Example 7: Use of Aromatic-Cationic Peptides in Treating Mitochondrial Iron Loading in Friedreich's Ataxia Mouse Model This example will demonstrate the use of aromatic-cationic peptides, such as D-Arg-2',6'-Dmt-Lys-Phe-$NH_2$, or a pharmaceutically acceptable salt thereof, such as acetate or trifluoroacetate salt, in treating mitochondrial iron loading in Friedreich's ataxia.

Mouse model. This example uses the muscle creatine kinase (MCK) conditional frataxin knockout mice described by Puccio et al., *Nat. Genet.* 27:181-186 (2001). In this model, the tissue-specific Cre transgene under the control of MCK promoter results in the conditional deletion of frataxin in only the heart and skeletal muscle.

Eight-week-old mutant mice are administered a daily dose of 0.25 mg/kg/day of D-Arg-2',6'-Dmt-Lys-Phe-$NH_2$ or saline vehicle only (control) subcutaneously for two weeks. Total RNA is isolated from hearts of two 10-week-old wild-type mice, two 10-week-old untreated mutant mice and two 10-week-old treated mutant mice. Total RNA is isolated using TRIzol (Invitrogen). First-strand cDNA synthesis and biotin-labeled cRNA are performed and hybridized to the mouse Affymetrix GeneChip 430 2.0. A 2-phase strategy is used to identify differentially expressed genes. First, genome-wide screening is performed using Affymetrix GeneChips. Then, low-level analysis is performed with Affymetrix GeneChip Operating Software 1.3.0, followed by the GC robust multiarray average (GCRMA) method for background correction and quantile-quantile normalization of expression. Tukey's method for multiple pairwise comparisons is applied to acquire fold-change estimations. Tests for significance are calculated and adjusted for multiple comparisons by controlling the false discovery rate at 5%.

Definitive evidence of differential expression is obtained from RT-PCR assessment of samples used for the microarray analysis and at least 3 other independent samples. Principal component analysis is performed by standard methods. Western blot analysis is performed using antibodies against frataxin (US Biological); Tfr1 (Invitrogen); Fpn1 (D. Haile, University of Texas Health Science Center); Hmox1 (AssayDesigns); Sdha, Gapdh, and Iscu1/2 (Santa Cruz Biotechnology); Fech (H. Dailey, University of Georgia, Biomedical and Health Sciences Institute); Hfe2 (S. Parkkila, University of Tampere, Institute of Medical Technology); Nfs1, Uros, and Alad (Abnova); Sec15l1 (N. C. Andrews, Duke University); F11, Fth1, Ftmt (S. Levi, San Raffaele Institute); and Hif1α (BD Biosciences).

For heme assays, hearts are exhaustively perfused and washed with PBS (0.2% heparin at 37° C.) to remove blood. After homogenization, heme is quantified using the QuantiChrom Heme Assay (BioAssay Systems). Tissue iron is measured via inductively coupled plasma atomic emission spectrometry For iron loading measurement assays, hearts are exhaustively perfused and washed with PBS (0.2% heparin at 37° C.) to remove blood. Mitochondria from the hearts are isolated using a mitochondrial isolation kit (Thermo Scientific, Rockford, Ill.). The iron concentration of the mitochondria is determined by the Ferene S-based Iron Assay Kit (BioVision, Milpitas, Calif.) according to the manufacturer's protocol.

It is anticipated that untreated mutant mice will exhibit decreased expression of genes involved in heme synthesis, iron-sulfur cluster assembly, and iron storage (FRDA Control) as compared to wild-type mice (Normal). However, it is anticipated that mutant mice treated with D-Arg-2',6'-Dmt-Lys-Phe-$NH_2$ will show expression levels that are similar to normal subjects with respect to genes involved in these three mitochondrial iron utilization pathways. It is further expected that administration of the present technology will have synergistic effects in this regard. It is also anticipated that mice treated with D-Arg-2',6'-Dmt-Lys-Phe-$NH_2$ will show an decrease in iron within the isolated mitochondria as compared to untreated mice.

These results will show that aromatic-cationic peptides of the present technology are useful in treating mitochondrial iron loading in Friedreich's ataxia or in subjects with lower frataxin expression or activity.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible sub-ranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for treating heart disease in a subject having Friedreich's ataxia, comprising administering to the subject a therapeutically effective amount of the peptide D-Arg-2',6'-Dmt-Lys-Phe-$NH_2$ or a pharmaceutically acceptable salt thereof.

2. The method of claim 1, wherein the peptide is administered daily for 6 weeks or more.

3. The method of claim 1, wherein the peptide is administered daily for 12 weeks or more.

4. The method of claim 1, wherein the heart disease comprises a condition selected from the group consisting of hypertrophic cardiomyopathy, myocardial fibrosis, and cardiac failure.

5. The method of claim 1, wherein the heart disease comprises hypertrophic cardiomyopathy.

6. The method of claim 1, wherein the heart disease comprises myocardial fibrosis.

7. The method of claim 1, wherein the heart disease comprises cardiac failure.

8. The method of claim 1, wherein the heart disease comprises a heart rhythm abnormality condition selected from the group consisting of tachycardia and heart block.

9. The method of claim 1, wherein the subject suffers symptoms selected from the group consisting of chest pain, shortness of breath, and heart palpitations.

10. The method of claim 1, wherein the subject is human.

11. The method of claim 1, wherein the peptide is administered orally, topically, systemically, intravenously, subcutaneously, intraperitoneally, or intramuscularly.

12. The method of claim 1, further comprising separately, sequentially or simultaneously administering to the subject one or more additional therapeutic agents selected from the group consisting of ACE inhibitors, digoxin, enalapril, or lisinopril, diuretics, beta blockers, idebenone, deferiprone, and insulin.

13. The method of claim 1, wherein the pharmaceutically acceptable salt comprises acetate or trifluoroacetate salt.

14. The method of claim 12, wherein administering the peptide and the additional therapeutic agent has a synergistic effect in the treatment of Friedreich's ataxia.

* * * * *